(12) United States Patent
Palmer et al.

(10) Patent No.: US 6,569,305 B1
(45) Date of Patent: May 27, 2003

(54) METHOD FOR INJECTION AND STACKING OF ANALYTES IN HIGH-CONDUCTIVITY SAMPLES

(76) Inventors: James Palmer, 268 Green Springs La., Gordonsville, VA (US) 22901; James P. Landers, 1966 Arbor Ct., Charlottesville, VA (US) 22911

( * ) Notice: Subject to any disclaimer, the term of this patent is extended or adjusted under 35 U.S.C. 154(b) by 0 days.

(21) Appl. No.: 09/418,659

(22) Filed: Oct. 15, 1999

(51) Int. Cl.[7] ................ G01N 27/26; G01N 27/447
(52) U.S. Cl. ................ 204/454; 204/450; 204/451
(58) Field of Search .................. 204/450–455, 204/549

(56) References Cited

U.S. PATENT DOCUMENTS

| | | | |
|---|---|---|---|
| 5,069,766 A | * | 12/1991 | Zhu et al. |
| 5,151,164 A | * | 9/1992 | Blanchard et al. |
| 5,358,612 A | * | 10/1994 | Dasgupta et al. |
| 5,391,274 A | * | 2/1995 | Shieh |
| 5,858,187 A | * | 1/1999 | Ramsey et al. |

OTHER PUBLICATIONS

Handbook of Capillary Electrophoresis, 2nd ed., pp. (1–47), (49–73), (717–739), CRC Press, Inc. (Unknown), (Feb. 1, 1997).

James F. Palmer, "Separation Characteristics of C21 Vertebrate Corticosteroids," A Thesis Submitted to the Graduate Division of the University of Hawaii in Partial Fulfillment of the Requirements for the Degree of Master of Science in Oceanography, Unknown (Unknown), (Dec. 1, 1997).

James Palmer, Nicole J. Munro, and James P. Landers, "A Universal Concept for Stacking Neutral Analytes in Micellar Capillary Electrophoresis," Analytical Chemistry News & Features, Analytical Division, Department of Chemistry, University of Pittsburgh (Pittsburgh, Pennsylvania), (May 1, 1999).

* cited by examiner

Primary Examiner—T. Tung
(74) Attorney, Agent, or Firm—Thorp Reed & Armstrong, LLP (57) ABSTRACT

The present invention is a method for injection and stacking of analytes in high salt samples. This stacking method works with both pressure injection or electrokinetic injection. The ability to stack analytes with electrokinetic injection allows the translation of high-salt stacking from the capillary to the microchip format.

82 Claims, 9 Drawing Sheets

METHOD FOR INJECTION AND STACKING OF ANALYTES IN HIGH-CONDUCTIVITY SAMPLES

BACKGROUND OF THE INVENTION

1. Field of the Present Invention

This invention relates to a method for injection and stacking of analytes in high salt samples. This stacking method works with both pressure injection or electrokinetic injection of high salt samples. This electrokinetic injection method allows for translation of high-salt stacking from the capillary to the microchip format.

2. Description of the Prior Art

Capillary electrophoresis (CE) is used for the analysis of a wide variety of compounds according to size and charge. CE is beneficial because it allows for high resolution separations while using miniscule amounts of both samples and reagents. However, neutral compounds cannot be separated in this mode because they have no charge. Therefore, micellar capillary electrophoresis (MCE) was pioneered to separate neutral and charged species.

MCE uses micellar solutions to separate neutral and charged species. The addition of a charged micelle solution in the separation buffer allows for hydrophobic interaction between neutral analytes and the electrophorectically-mobile micelle phase which can afford separation. However, in MCE (as in all CE modes), the total capillary volume is typically in the microliter range. Therefore injection lengths are limited by the micrometer dimensions of the capillary to the millimeter range. As a result it is critical to develop sample stacking schemes which allow for longer injections without a loss of resolution of analytes.

However, sample stacking in MCE oftentimes proves problematic as most known stacking methods require a particular combination of micelle type, sample pH, electroosmotic flow rate, and separation-mode polarity. Further, the difference in ionic strength between separation buffer and sample matrix is oftentimes achieved by diluting the sample, which compromises resolution. The need exists for a simple, more universal stacking method not limited to micelle type, sample pH, electroosmotic flow rate, and separation-mode polarity. The need also exists for a stacking method useful for neutral species.

SUMMARY OF THE INVENTION

The present invention is directed to a method of preparing a device for electrophoresis which includes the step of achieving a desired conductivity in a sample of analytes through any appropriate mechanism. Such mechanisms can include the addition of salts, the addition of conductive species not considered to be salts, the addition of pH buffers, the addition of conductive species having a higher electrophoretic mobility than that of the buffer ions, the elimination of organic modifiers (which decreases conductivity), the utilization of naturally high-conductivity samples and the dilution of high-conductivity by the addition of organic modifiers or water. The conductivity of the sample analytes is measured relative to a buffer, in which electrophoretic separation occurs. The desired conductivity of the sample of analytes may be achieved by modifying the characteristics of the buffer through any appropriate mechanism. Such mechanisms can include the reduction or elimination of salts, the reduction or elimination of conductive species not considered to be salts, the reduction or elimination of pH buffers, the maintenance, addition, or elimination of conductive species with electrophoretic mobility which are lower than the mobility of the sample matrix conductive species, the addition of organic modifiers, or the addition of conductive species.

A plug of the sample is injected either through pressure or by applying an electric field into a capillary (a filament type of device), a microchannel on a microchip, or any other type of device in which electrophoretic separation can occur.

An electric field is applied which causes field amplification in the separation buffer. That causes stacking of buffer ions against the sample which subsequently causes stacking of the sample components. Stacking of the sample components is believed to cause reverse isotachophoresis due to the higher mobility anion in the sample matrix occurring at a higher concentration than the separation buffer ion. That causes stacking of the separation buffer ion against the sample which subsequently causes stacking of the sample components. When the sample is electrokinetically injected, the foregoing processes begin during electrokinetic injection and continue after the electrokinetic injection is completed.

One benefit of the present invention is that it provides a method of stacking that is independent of the pH, micelle type, electroosmotic flow, and separation-mode polarity. This method is also applicable to a wide variety of buffer systems and does not require sample dilution.

Electrokinetic injection is counterintuitive because a neutral analyte will have no electrophoretic mobility in an electric field in the absence of a carrier vector such as a micelle. Therefore electroinjection of neutral analytes without a carrier vector is a novel benefit of the present invention. This method of the present invention, that is, utilizing electroinjection, is potentially more than an order of magnitude more powerful for concentrating neutral analytes than prior art mechanisms.

Additionally, as the present invention can utilize electrokinetic injection, it allows translation of high-salt stacking from the capillary to the microchip format. The method of the present invention can be translated directly to the microchip format with existing channel technology, that is, a simple separation channel with a cross-T injection channel. It is possible to utilize the microchip format because the present invention may be driven electrokinetically, which is currently the only practical mode of sample injection on the microchip format. Those, and other advantage and benefits of the present invention will become apparent from the Detailed Description of the Preferred Embodiment herein below.

BRIEF DESCRIPTION OF THE DRAWINGS

For the present invention to be easily understood and readily practiced, the invention will be described, for purposes of illustration and not limitation, in conjunction with the following figures wherein.

DETAILED DESCRIPTION OF THE PREFERRED EMBODIMENT

Figure 1:
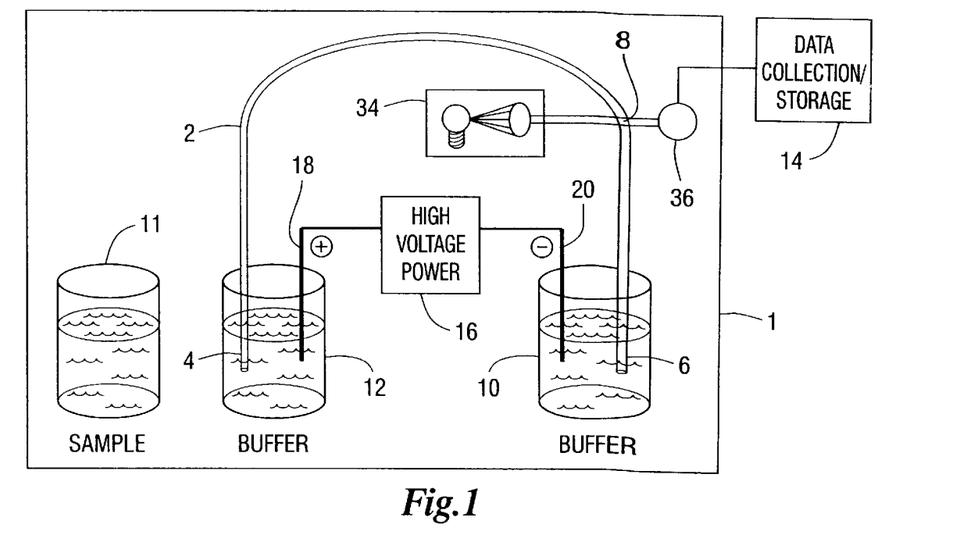
FIG. 1 is a test setup used to practice the method of the present invention.

FIG. 1 shows one test setup which can be used to practice the method of the present invention. Electrophoresis unit 1 is interfaced with data collection/storage unit 14, which contains software for control of the instruments and data collection. Separation channel 2 (shown as a capillary) has an entrance end 4, an exit end 6, and a detection window 8. Separation channel 2 is rinsed by high pressure with a three to five capillary volume of buffer. Outlet reservoir 10 is filled with buffer and holds exit end 6 of separation channel 2. Inlet reservoir 12 is also filled with buffer and holds entrance end 4 of separation channel 2. Sample reservoir 11 contains sample for injecting into separation channel 2. High voltage power unit 16 has an anode 18 and a cathode 20. Outlet reservoir 10 also holds cathode 20, while inlet reservoir 12 also holds anode 18.

Figure 2:
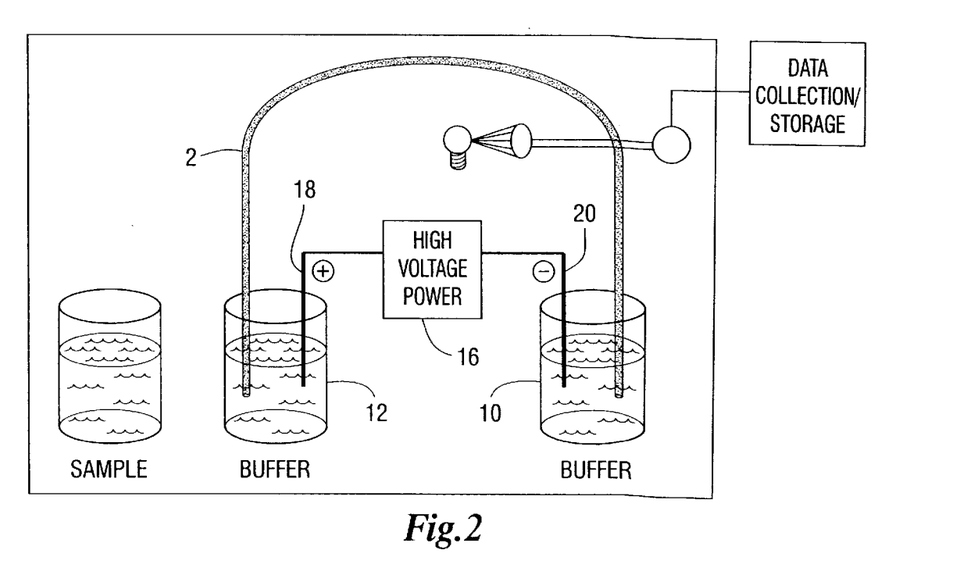
FIG. 2 is a test setup used to practice the method the present invention which shows an electric field being applied across the separation channel for electrophoretic conditioning.

As shown in FIG. 2, an electric field is then applied by high voltage power unit 16 across separation channel 2 from anode 18 to cathode 20, which causes buffer in inlet reservoir 12 to travel through separation channel 2 and into outlet reservoir 10, for electrophoretic conditioning of separation channel 2.

Figure 3:
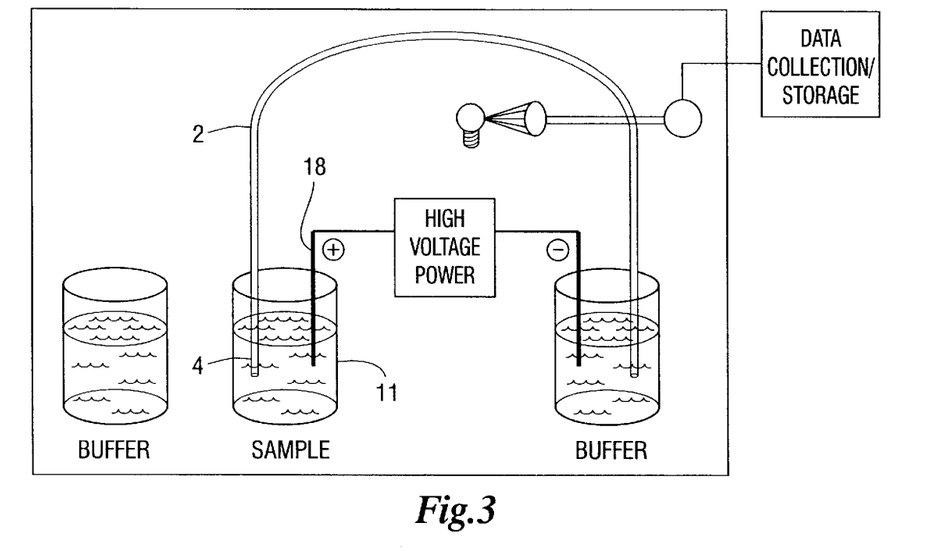
FIG. 3 is a test setup used to practice the method of the present invention after the separation channel has been electrophoretically conditioned.
Figure 4:
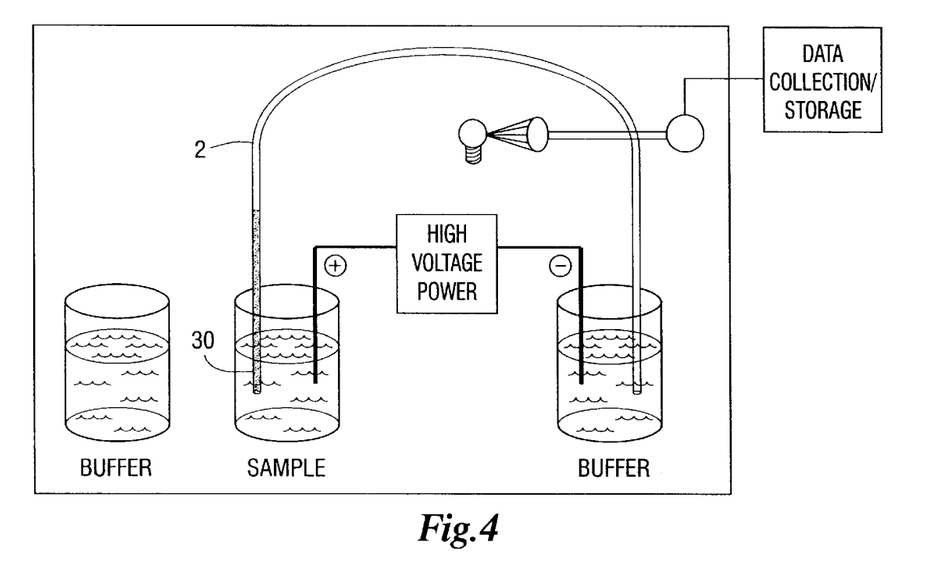
FIG. 4 is a test setup used to practice the method of the present invention, which shows an electric field being applied across the separation channel for electrokinetic injection of a sample plug into the separation channel.

As shown in FIG. 3, after separation channel 2 has been electrophoretically conditioned, anode 18 and entrance end 4 of separation channel 2 are placed within sample reservoir 11. FIG. 4 shows an electric field being applied across separation channel 2 for electrokinetic injection of a sample plug 30 into separation channel 2. The electric field is applied across separation channel 2 for a period of time sufficient to permit injection of a sample plug 30 of a desired length. Alternatively, the plug 30 could be injected into separation channel 2 using a pressure technique known in the art. It is known that the length of the plug 30 should be a substantial portion of the channel 2 to provide an adequate volume of analyte for separation and thus providing for easier detection. The length of the plug can actually exceed the functional length, i.e. the length to the detector, of the capillary in those cases where the stacking analytes have a lower velocity than the EOF. With long plugs, there will be less time for electrophoretic separation before the leading edge of the plug reaches the detector. This can actually be advantageous when examining low velocity analytes. While the technique of pressure injection may be used with a capillary type of separation channel 2, for separation channels fabricated on microchips, electrokinetic injection is the only practical mode of injection as discussed in greater detail in the experimental results hereinbelow.

Figure 5:
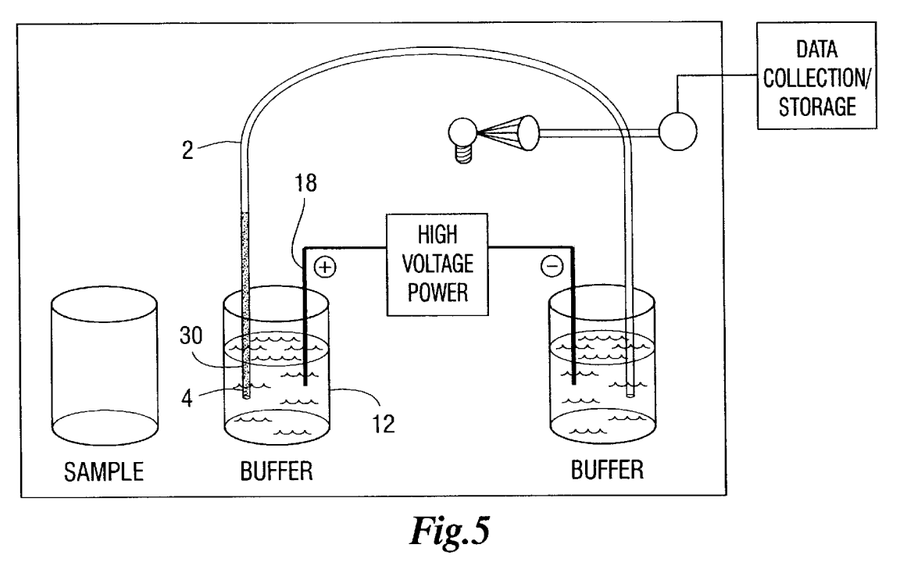
FIG. 5 is a test setup used to practice the method of the present invention after electrokinetic injection of a sample plug.

As shown in FIG. 5, after sample plug 30 is injected into separation channel 2, entrance end 4 of separation channel 2 and anode 18 are placed within inlet reservoir 12.

Figure 6A:
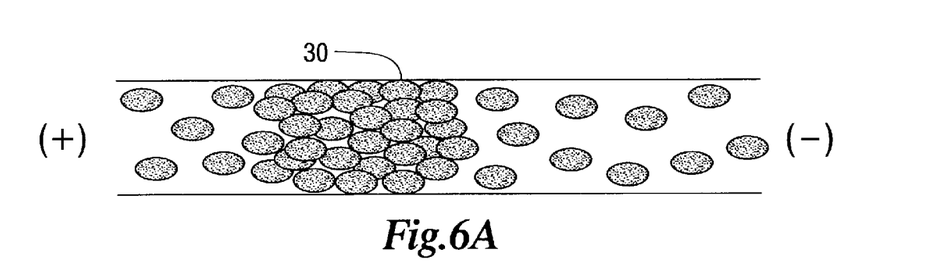
FIGS. 6a, 6b and 6c show, in a time progression series, a proposed mechanism of high-salt stacking and separation of the present invention.
Figure 6B:
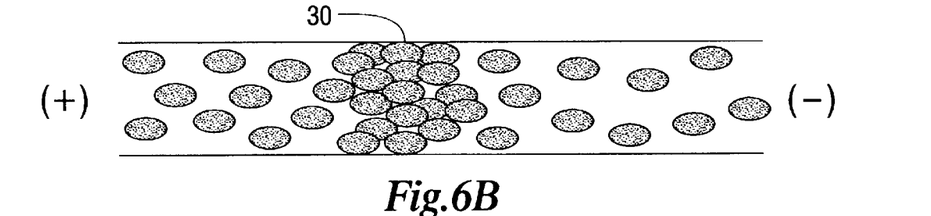
Figure 6C:
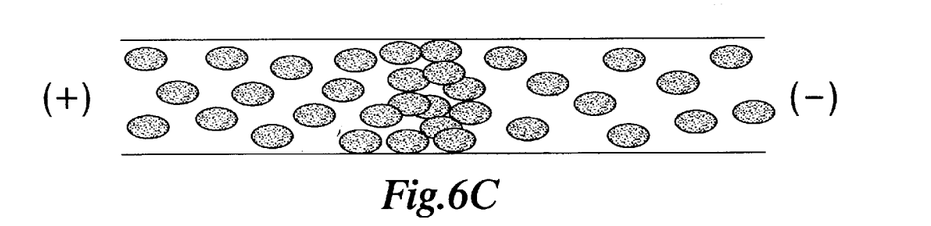

FIGS. 6a, 6b and 6c show, in a time progression series, a proposed mechanism of high-salt stacking and separation of the present invention. FIG. 6a shows a proposed mechanism of the sample plug 30 as the electric field is initially being applied. FIG. 6b shows the sample plug 30 at a later time, with micellar stacking evident. FIG. 6c shows the sample plug 30 at a time later than that represented in FIG. 6b, where micellar stacking and separation is evident. A more complete description of FIGS. 6A, 6B, 6C is found in Palmer J.; Munro, N.; Landers, J., *Anal. Chem.* 1999, 71, 1679–87 which is hereby incorporated by reference.

Stacking of neutral analytes in MCE with a sample matrix devoid of electokinetic vectors is analogous to HPLC stacking injections. In HPLC, the injected analyte is stacked if its velocity is decreased at the detector side of the zone, which occurs during sample loading as the velocity of the analyte in the sample solvent is decreased by the stationary phase. It is also stacked from the injection side, when the separation solvent is sent down the column. The separation solvent accelerates the sample plug from the injection end by removing it from the stationary phase. Stacking is proportional to the velocity difference between the zones in either case.

In MCE, the nomenclature is reversed. That is, the solvent is the stationary phase and the micelle is the mobile phase, but concepts for analyte stacking are the same. Because the micelle is mobile, it is sometimes referred to as the pseudo stationary phase. EOF can be disregarded as a differential mobility vector, as the mobility it imparts is distributed to all components (neutral, charged positively, or negatively) to an equal extent. In this context, an analyte (in MCE) injected in a sample matrix consisting of an aqueous phase devoid of an electrokinetic vector cannot be "stacked" unless the velocity of the analyte in the sample plug is either decreased from the detector side, or increased from the injector side.

The velocity of a neutral analyte in MCE (disregarding EOF and wall interactions) is affected only by interaction with a charged carrier. The mobility of the analyte/charged micelle complex must obey the rules set forth earlier for stacking to ensue. Maximum analyte peak height is not dependent upon narrowing of the analyte zone, but upon obtaining the highest concentration of analyte possible. When a long sample plug is injected, concentration is dependent upon the portion or percent of analyte that a pseudostationary phase can advance from one incremental zone to the next (plate height). Neutral analytes are increased in concentration to the point that the portion of analyte left behind at each step is equal to the initial concentration of the sample zone. After maximum concentration is reached (with extended injections), the analyte peak should broaden in a non-Gaussian fashion, with flat peak tops exhibiting the maximum concentration possible, and peak width subsequently increasing linearly with injection length.

When zones with different conductivities are injected into the capillary, the total EOF is a hybrid of the two individual solution EOF's. With high-salt stacking, the EOF velocities for the high-salt sample matrix and the separation buffer are in a range (of approximately 90 to 200 mM sodium) where differences should be minimal.

The electrokinetic injection via EOF of neutral analytes in high salt sample matrixes is utilized to facilitate stacking in MCE. The high salt-stacking mechanism also operates with the electrokinetic injection of the neutral analytes directly from the high-salt sample reservoir. In this case, the only velocity imparted to analytes within the sample matrix would be due to EOF. The rate of delivery of neutral analytes would be proportional to EOF velocity during electrokinetic injection. The high-salt matrix in the sample vial induces the same phenomenon of micelle stacking as is observed with a pressure injection. However, instead of using valuable capillary length for the pressure injection, the stacking process is now initiated at the inlet of the capillary.

Figure 7:
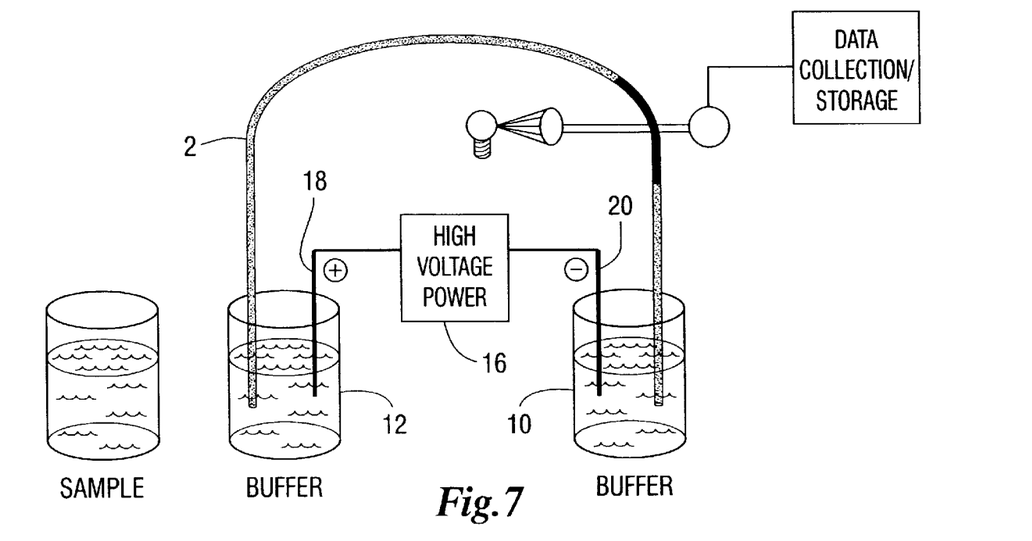
FIG. 7 is a test setup used to practice the method of the present invention which shows an electric field being applied across the separation channel causing separation and detection of separation at time t3.

FIG. 7 shows plug 30 located at detection window 8. Radiation, for example from UV source 34, shines through detection window 8 and therefore through the analytes and is detected by detector 36 located on the opposite side of detector window 8 from UV source 34. Detector 36 is interfaced with data collection/storage unit 14 to collect separation data.

Figure 8:
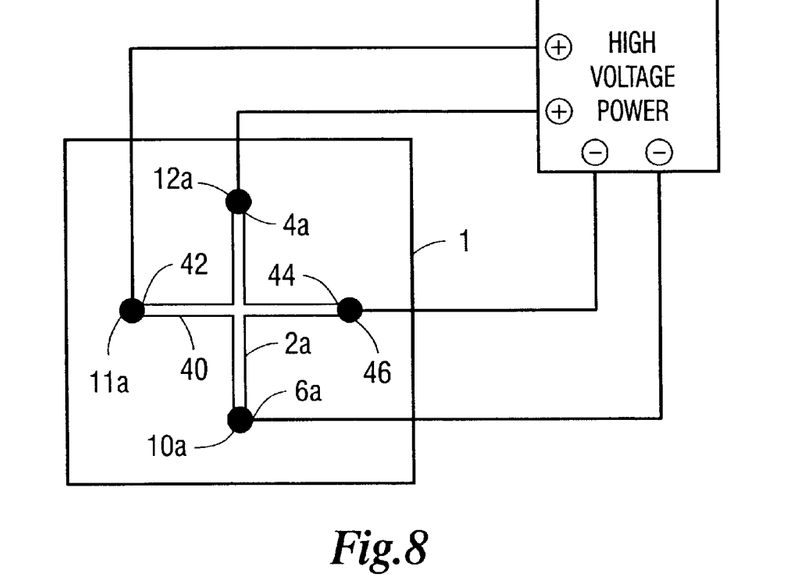
FIG. 8 is a test setup used to practice the method of the present invention.

FIG. 8 is a test setup used to practice the method of the present invention, wherein electrophoretic unit 1 is a T-configuration cross-channel injection microchip. Separation channel 2a has an entrance end 4a, an exit end 6a. Outlet reservoir 10a is filled with buffer and is connected to exit end 6a of separation channel 2a. Inlet reservoir 12a is also filled with buffer and is connected to entrance end 4a of separation channel 2a. Sample channel 40 has an entrance end 42 and an exit end 44. Sample reservoir 11a contains sample for injecting into separation channel 2a and is connected to entrance end 42 of sample channel 40. Waste reservoir 46 is filled with buffer and is connected to exit end 44 of sample channel 40. Sample channel 40 is configured to connect with and cross over separation channel 2a to form a T-configuration. High voltage power unit 16a has an anode (not shown) connected to inlet reservoir 4a and an anode (not shown) connected to sample reservoir 11a, and a cathode (not shown) connected to outlet reservoir 10a and a cathode (not shown) connected to waste reservoir 46.

Figure 9:
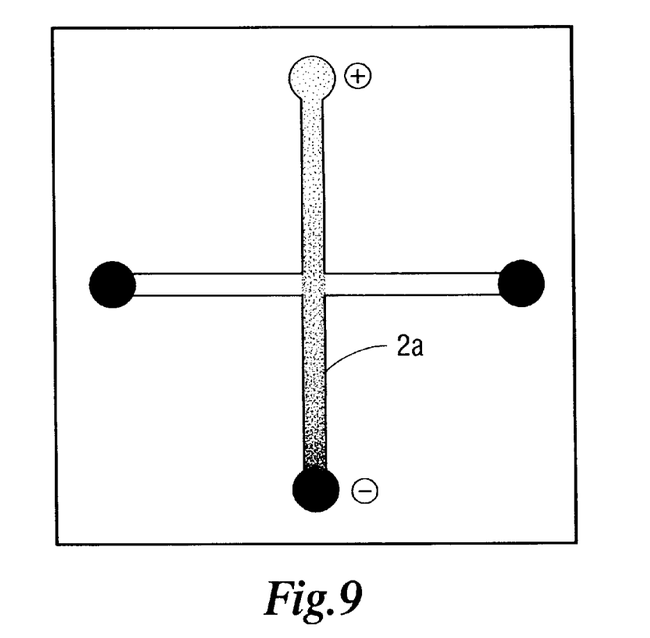
FIG. 9 is a test setup used to practice the method of the present invention which shows an electric field being applied across the separation channel for electrophoretic conditioning.

FIG. 9 shows an electric field being applied across separation channel 2a for electrophoretic conditioning. The field is applied from the anode (not shown) connected to inlet reservoir 12a to cathode (not shown) connected to outlet reservoir 10a.

Figure 10:
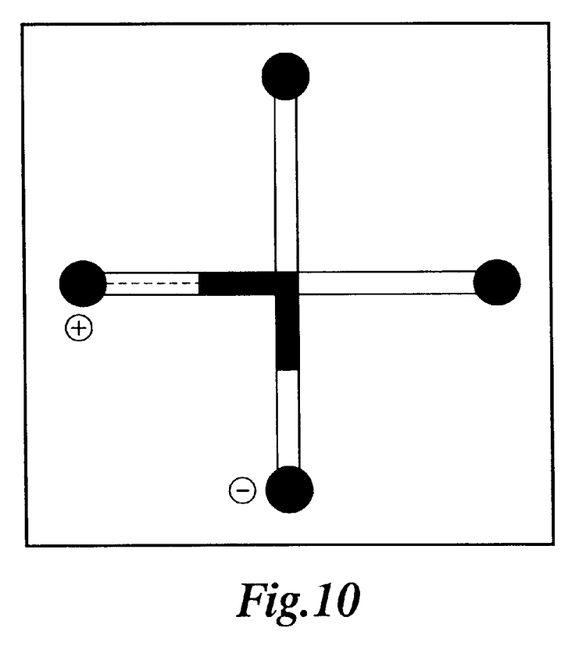
FIG. 10 is a test setup used to practice the method of the present invention, which shows an electric field being applied from the sample well to the outlet reservoir for electrokinetic injection of a sample plug into the separation channel.

FIG. 10 shows an electric field being applied from the anode (not shown) connected to sample reservoir 11a to cathode (not shown) connected to outlet reservoir 10a for electrokinetic injection of a sample plug into separation channel 2a.

Figure 11:
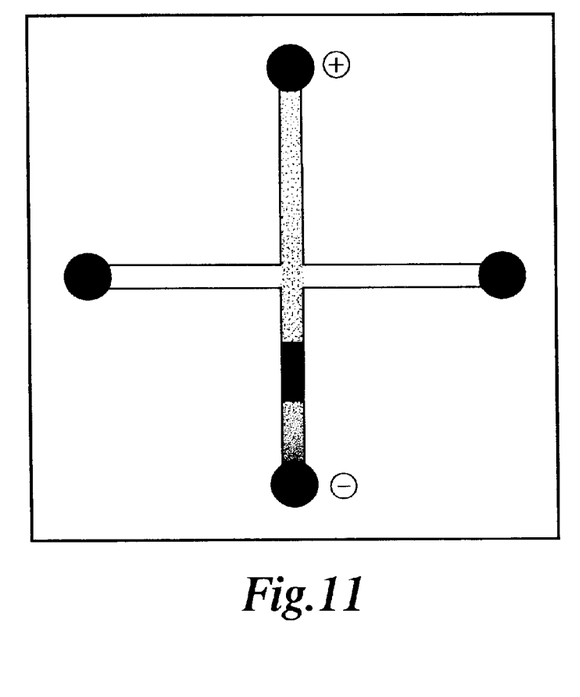
FIG. 11 is a test setup used to practice the method of the present invention which shows an electric field being applied across the separation channel causing separation and detection of separation.

FIG. 11 shows an electric field being applied across separation channel 2a causing separation and detection of separation. The field is applied from anode (not shown) connected to inlet reservoir 12a to cathode (not shown) connected to outlet reservoir 10a.

Experimental Results

Electrokinetic versus pressure injection offers a decrease in injection times of more than an order of magnitude with smaller-ID capillaries. In order to compare electrokinetic versus pressure injection, the rate of neutral marker flow under both electrokinetic and pressure injections was determined for capillaries of various ID's and lengths. The effect of salt concentration in the sample matrix was examined. Equivalent plug length was compared for electrokinetic and pressure injections. The effect of field strength during injection was also examined. Resolution of equivalent plug lengths and plug volumes for electrokinetic versus pressure injections were examined for capillaries of different ID's.

In smaller-ID capillaries, particularly microchip channels, complete control of EOF is strongly indicated for ease of automation and rapid analysis. To demonstrate stacking on the microchip format, a neutral analyte was separated from EOF in MCE mode in a standard capillary with fluorescence detection. The analyte was subjected to high-salt stacking on a simple T-design cross-channel injection chip in MCE mode.

Materials:

HPLC-grade water was obtained from Fisher (St. Louis, Mo.) and was used for all separation buffers and sample matrixes. Sodium tetraborate, sodium hydroxide, sodium chloride, punctilious ethanol, and potassium sulfate were obtained from Sigma (St. Louis, Mo.). Cholic acid, sodium salt hydrate, was obtained from Aldrich Chemical Company (Milwaukee, Wis.). Corticosteroids were obtained from Steraloids, Inc. (Newport, R.I.). BODIPY (4,4-difluoro-5,7-dimethyl-4-bora-3a, 4a-diaza-s-indacene-3-propanol) was obtained from Molecular Probes, (Eugene, Oreg.), and sodium flourescein was obtained from Acros (New Jersey). The 17-hydroycorticosteriods exhibit a useful spectrum of velocities with the cholate micelle system. The relative affinity of these analytes for cholate is strongly indicated as due to hydrophobic interaction alone and their differential response to stacking reveal much about the actual mechanism.

Standard Capillary Apparatus:

Experiments were conducted wherein electrophoresis unit 1 was a Hewlett Packard HPCE-3D machine interfaced with data collection/storage unit 14, which is a Hewlett Packard Kayak XA computer with HP 3D-CE ChemStation Rev. A.06.01[403] software for control of the instrument and data collection. The separation channels 2 were bare silica, polyamide surfaced, capillaries of either 19, 27, or 49 $\mu$m internal diameter (ID) and approximately 370 $\mu$m outer diameter (OD). These capillaries can be purchased from Polymicro Technologies, Incorporated, (Phoenix Ariz.). The separation channel 2 temperature was maintained at 20° C. and detection (by detector 36) was by UV absorbance at 242 nm with a 20 nm bandwidth.

Stacking of a fluorescent neutral compound was performed with a Beckman P/ACE 5510 with a P/ACE system laser module 488 and a 27 $\mu$m by 37 cm capillary. EOF was identified with the capillary placed in an UV detection cartridge, and the LIF detector on the P/ACE was replaced with a standard UV detector (detector wavelength 254 nm). Buffer and sample preparation were as listed below for the corticosteroid concentrations, with analytes at 100 nM in 150 mM sodium chloride. Injections were carried out from 1 to 64 seconds at 30 kV, with peak height for BODIPY linear with injection lengths from 4 to 32 seconds ($R^2$=0.9977), with continued peak height increase at 64 seconds ($R^2$=0.9842).

Buffer and Sample Preparation

Separation buffers consisted of 80 mM sodium cholate, 5 mM tetraborate, and 10% punctilious ethanol in HPLC-grade water (pH range 8.9–9,1). Buffers were degassed by manual decompression in a syringe and passed through a 0.2 $\mu$m filter before use. Sample matrixes were prepared with sodium chloride at stated concentrations in HPLC-grade water. Crystalline corticosteroids were dissolved in punctilious ethanol at 1.00 $\mu$M (316 to 362 $\mu$g/ml). Aliquots were dried down and resuspended at stated dilutions. Standards were stored at 4° C. when not in use. Analyte concentrations were 10 $\mu$g/ml for all experiments except where noted.

Capillary Electrophoresis Conditions:

Capillary length was 33 or 48.5 cm, with an ID of 49 $\mu$m for most experiments except as noted. New capillaries were conditioned by rinsing with 1.0 M sodium hydroxide, water, and separation buffer, in that order. The same procedure was used to rinse the capillaries at the start and finish of each day's experiments. For all separations, the capillary was first rinsed by high pressure (approximately 950 mbar) with a three- to five-capillary volume of fresh separation buffer (1–5 minutes). Separation was carried out at 30 kV unless otherwise stated. The electrophoresis buffer was replenished after no more than 2 hours total running time and the capillaries were reconditioned daily by flushing with 1.0 M sodium hydroxide and water.

Sample Matrix and Sample Injection Parameters:

Sample matrix was 150 mM sodium chloride unless otherwise stated. Relative conductivity of solutions was gauged. Rate of sample delivery by pressure and electrokinetic injection were determined for 33 cm capillaries with ID's of 19, 27, and 49 $\mu$m, and for the 49 $\mu$m capillary with lengths of 48.5 and 64.5 cm. Triplicate injections were made from a 150 mM sodium chloride solution under reverse pressure (−50 mbar) or voltage (−30 kV) from the outlet vial, which contained the high-salt matrix. Time of absorbance shift at the detector window (distance 8.5 cm) during injection was recorded.

Sample matrixes consisting of 0 to 300 mM sodium chloride were examined for stacking effect during electrokinetic injection at 30 kV for 40 seconds. Equivalent plug-length injections for pressure and electrokinetic injection were compared from 20 to 160 seconds (50 mbar) and 5 to 40 seconds (30 kV). Analytes in 150 mM sodium chloride were electrokinetically injected at a constant of 1200 kV seconds, that is, 1,2,4,8,16 and 30 kV for 1200, 600, 300, 150, 75, and 40 seconds, respectively, to determine effect of field strength during injection on ultimate resolution of analytes. Resolution of analytes in both equivalent plug lengths and plug volumes were compared for different capillary ID's. Effect of pH of the sample matrix was previously determined to be unimportant with the selected analytes. However, hydrolysis of the sample matrix is severe with low-ionic strength buffers. To increase reproducibility for repeat injections, it is indicated that a buffer salt should be used instead of sodium chloride in the sample matrix.

Stacking on a Chip:

A simple T-configuration cross-channel injection microchip (Alberta Microelectronics Corporation, Edmonton, Alberta, Canada) was utilized to demonstrate stacking of neutral analytes on a microchip format. The channel plate was 1.1 mm thick, and the cover plate was 1.75 mm thick, both made of Borofloat glass (Schott Optical Glass). The separation channel was 8.6 cm long, with a hemispherical cross section 50 $\mu$m wide by 20 $\mu$m deep. The sample T-channel was the same cross dimensions as the separation channel, extending perpendicular to the separation channel for 0.6 cm to the sample and waste.

An apparatus for pressure-flushing of a microchip by an HPLC pump and subsequent electrophoresis was utilized that has been previously described. The microchip channels (that is, separation channel 2a and sample channel 40) were conditioned with sodium hydroxide and water by flushing with sodium hydroxide and water. Separation buffer was then flushed through all channels. The sample reservoir 11a was rinsed with 150 mM sodium chloride by disposable pipette several times, and then filled with the sample matrix of 150 mM sodium chloride and BODIPY at approximately 70 nM. Inlet, outlet, and waste reservoirs 12a, 10a, 46, respectively, were filled to equivalent level with separation buffer. Air bubbles or particles visible in each of inlet reservoir 12a, outlet reservoir 10a and/or waste reservoir 46 were removed prior to electrophoresis. Electrophoretic conditioning of separation channel 2a was commenced by inducing a field between the inlet reservoir 12a and outlet reservoir 10a (+500/−2000) for 100 seconds, while holding sample reservoir 11a and waste reservoir 46 at ground to reduce leakage. Electrokinetic injection was performed by applying an electric field between sample reservoir 11a and outlet reservoir 10a (+250/−1000) for 20 to 120 seconds, while floating waste reservoir 46 and inlet reservoir 12a. Separation mode was initiated by redirecting the electric field from inlet reservoir 12a to outlet reservoir 10a (+500/−2000), with sample reservoir 11a and waste reservoir 46 at ground.

Results and Discussion

Electokinetic injection was investigated over a range of conditions to determine the optimal characteristics for its application to MCE neutral analyte sample concentrating.

Rate of Electrokinetic or Pressure Injection:

With neutral analytes, the total analyte delivery into the capillary (plug length) can be equated between electrokinetic and pressure injections. During electokinetic injection, a sample matrix with a conductivity 2 to 3 times that of the separation buffer should supply all components in the sample vial to the capillary inlet at a rate due to diffusion, not electrophoretic mobilities. This is due to the greatly reduced electric field in the sample vial versus the capillary, analogous to the principle used for electrochemical detection of analytes in CE mode. In this case, EOF velocity multiplied by time would give a plug length for electrokinetic injections. The rate at which the EOF marker (neutral sample components) in the sample matrix reached the detector under electrokinetic injection was compared to the appearance of the neutral marker during pressure injection. Table 1 shows the results for different capillary ID's as well as capillary length for the 49 $\mu$m capillary. Depending on the capillary diameter, electrokinetic injection can be more than an order of magnitude faster than pressure injection.

| ID/Length | Pressure (50 mbar) | cm/s @30 kV |
|---|---|---|
| 19/33 | .0119 cm/s | .295 |
| 27/33 | .023 cm/s | .301 |
| 49/33 | .081 cm/s | .267 |

Figure 12:
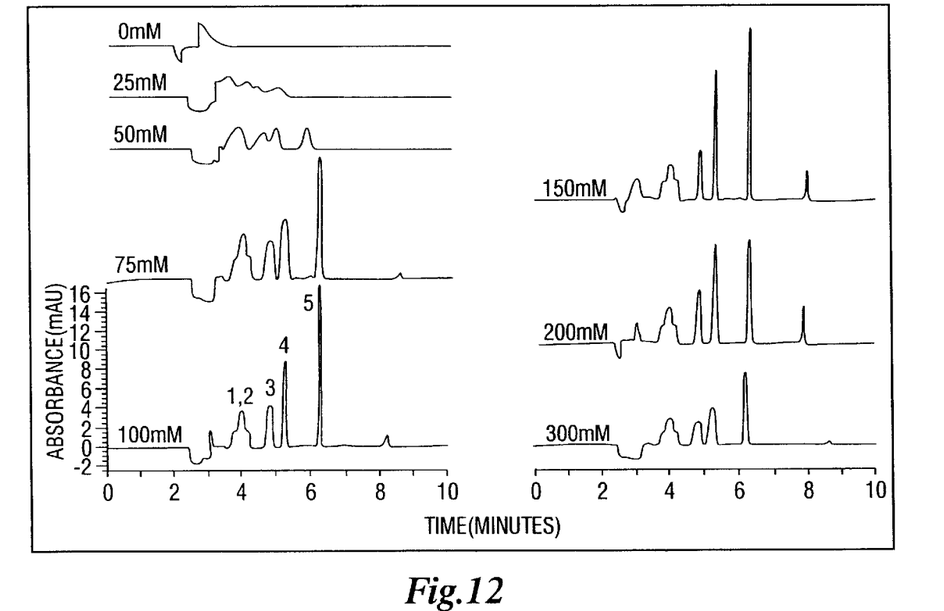
FIG. 12 is an absorbance v. time graph which shows the stacking effect at different sample matrix conductivities, that is, at different sample matrix concentrations.
Figure 13:
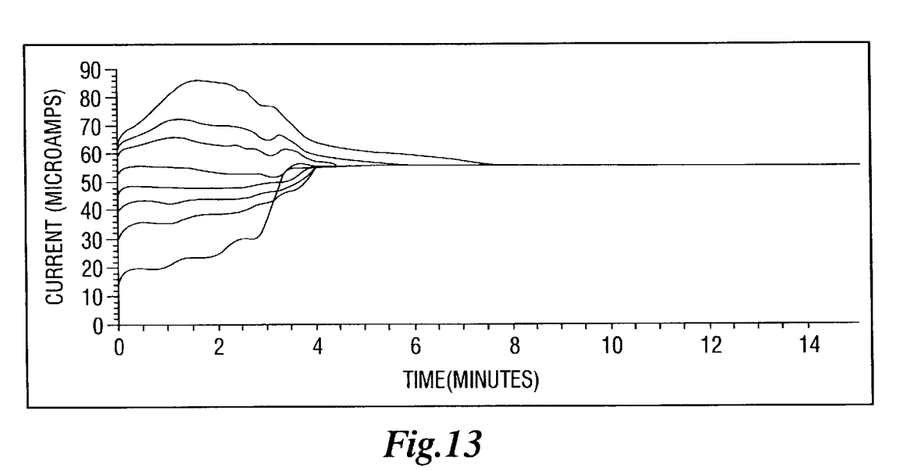
FIG. 13 is a current v. time graph which shows the current traces during electrophoresis to indicate the effect of sample matrix conductivity on the MCE system.

Salt Concentration:

The effect of salt concentration in the sample matrix was investigated. Analytes were dried down and reconstituted in salt matrixes ranging from 0 to 300 mM sodium chloride. Results are shown in FIG. 12. Salt concentration in the sample matrix of 0 to 25 mM have a conductivity below that of the separation buffer. Separation of the analytes is not clear at these concentrations, and sample concentration is not evident. At 50 mM, the sample matrix has approximately the same conductivity as the separation buffer, yet there is negligible sample concentration. However, when the conductivity of the sample matrix is raised substantially above that of the separation buffer (75 mM and higher), analyte resolution is sharply increased. An examination of the current traces during electrophoresis indicates the effect of sample matrix conductivity on the MCE system, as shown in FIG. 13.

Figure 14:
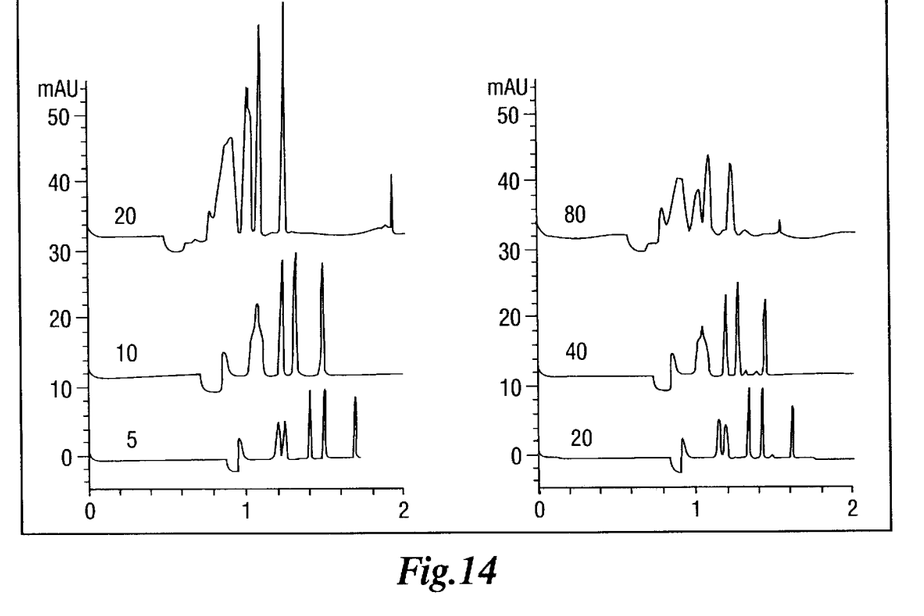
FIG. 14 sows an absorbance v. time graph for electrokinetic injection on the left as compapred to an absorbance v. time graph for pressure injection on the right.

Electrokinetic Injection Versus Pressure Injection:

Effect of injection length was made with a sample matrix of 150 mM sodium chloride, for electrokinetic injection at 30 kV from 5 to 40 seconds, and for pressure injection from 20 to 160 seconds with the 49 $\mu$m by 33 cm capillary. As can be seen in FIG. 14, the analytes "top out" in concentration at different injection lengths according to their affinity for the MCE system. However, this does not mean that the system is not capable of longer injections with higher affinity analytes. The system does not fail until peak heights begin to decrease. With pressure injections, a functional peak maximum is reached at 80 seconds for progesterone, with peak height approximately ⅓ that of the equivalent electrokinetic injection (20 seconds). It can be inferred that injections can be carried out for most of the effective length of the capillary with electrokinetic injections (40 second electroinjection is 11 seconds away from the detector window, and shows a peak height increase of 1.5 times for progesterone via pressure injection).

Figure 15:
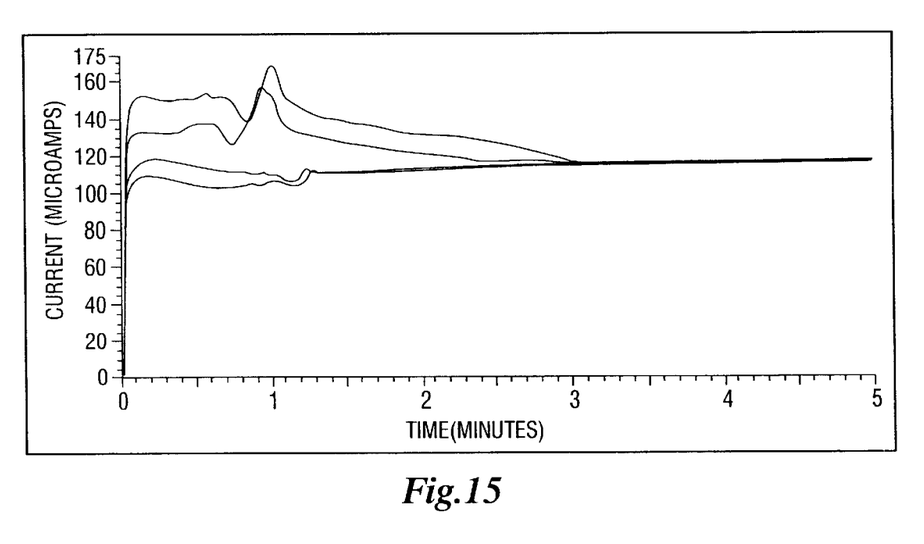
FIG. 15 is a current v. time graph which shows current traces for electrokinetic and pressure injections.
Figure 16:
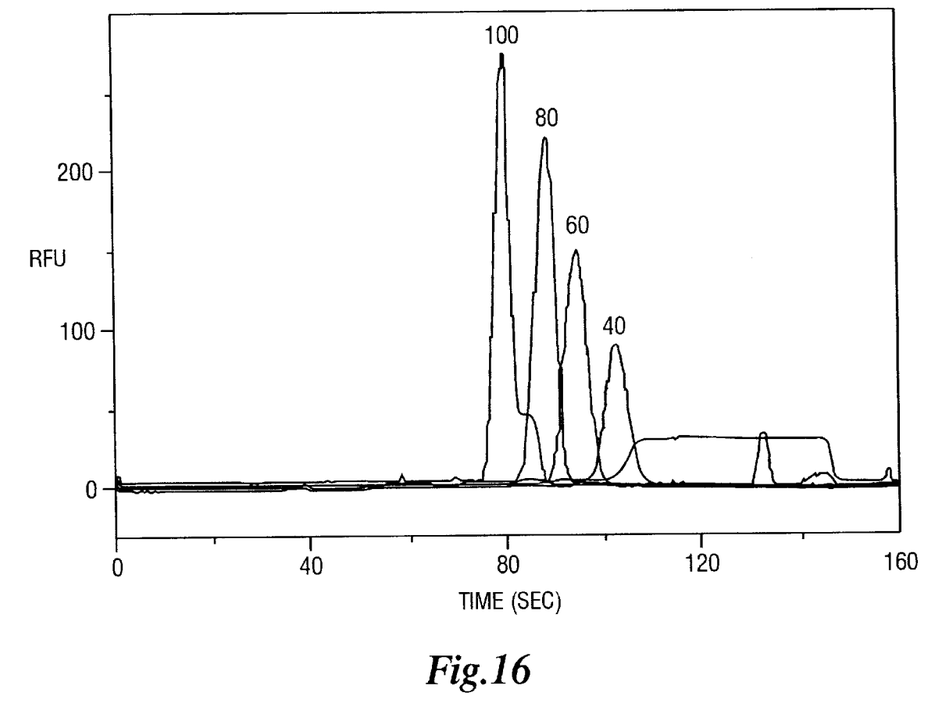
FIG. 16 shows stacking effects of a neutral analyte on a microchip.

FIG. 15 shows the effect on current by the two injection techniques. There is substantially lower current with electrokinetic versus pressure injection. This may be explained by the initiation of the stacking process at the capillary inlet with electrokinetic injection of the high-salt matrix, as opposed to initiation at the point in the capillary at which the sample matrix meets the separation buffer under pressure injection.

Effect of Field Strength During Electrokinetic Injection:

Different conductivity zones within the capillary during separation, whether introduced by electrokinesis or pressure, induce effects which can either narrow or broaden analyte zones. The effect of electrokinetically-injected high-salt zones in MCE was examined by comparing equivalent electrokinetic injections at varied potentials.

The effect of the injection field was examined by varying the kilovolts applied by the injection time. A constant of 1200 kV seconds was used. For instance, a 1 kV injection lasted 1200 seconds, 2 kV lasted 600 seconds, and so on to the 30 kV injection for 40 seconds. There is a negligible difference in peak height with a 1 kV and 30 kV injections. However, the higher voltage is accompanied by slight peak broadening, as evidenced the maximum plates per meter being 1,700,000 and 540,000 for the 1 kV and 30 kV injections, respectively. It can be assumed the peak broadening (lower plate number) is from diffusion at the fringes of the analyte zone, not to failure of the high-salt concentration method. The slight broadening of peaks with the higher fields is presumably due to joule heating, but the tremendous decrease in injection times as well as the maintenance of the maximum concentration (peak height) makes the highest voltage injection a desirable option.

Electrokinetic Injection and Stacking on a Microchip:

Stacking on a chip with the neutral fluorescent analyte BODIPY was performed. First, the analyte was stacked with a standard capillary apparatus to determine feasibility. Using a simple cross-T microchip, it was possible to emulate the capillary injection method by placing separation buffer in the inlet reservoir 12$a$, outlet reservoir 10$a$, and waste reservoir 46, with the high-salt sample matrix placed in the sample reservoir 11$a$, as shown in FIG. 8. By directing the field from the sample reservoir 11$a$ to the outlet reservoir 10$a$, electrokinetic injection of the high-salt sample matrix was initiated. Injections of 20 to 120 seconds were successfully made. When the analyte was injected out of a sample matrix consisting of separation buffer, stacking is not evident.

Conclusions

The electrokinetic stacking of neutral analytes in a sample matrix devoid of an electrokinetic vector for MCE separation has been demonstrated in the test results. The concepts used to achieve this stacking, i.e., (1) use of a sample matrix ion with a higher electrophoretic mobility and sufficiently higher concentration than the separation buffer ion such that the velocity (overall rate at which the analyte moves toward the detector) of the sample matrix ion is reduced below that of the separation buffer ion, and (2) utilizing a sample matrix conductivity substantially above that of the separation buffer, are concepts which should be broadly applicable to many if not all modes of electrophoresis. An example of this is the immediate translation of this method to the microchip format. Another example is the applicability of the present invention to the electrophoresis of charged analytes wherein the relative electrophoretic mobility of the analytes is controlled such that the velocity of the sample matrix ion is reduced below that of the separation buffer ion while utilizing a sample matrix conductivity substantially above that of the separation buffer. Yet another example is the use of particles other than micelles as the pseudo-stationary phase.

Although the present invention has been described in conjunction with preferred embodiments thereof, those of ordinary skill in the art will recognize that many modifications and variations may be made. The following claims are intended to cover all such modifications and variations.

What is claimed is:

1. A method, comprising:

filling a device with a separation buffer having a pseudo-stationary phase;

increasing the ionic strength of a sample of analytes relative to the separation buffer so that the ionic strength of the sample of analytes is equal to or greater than the ionic strength of the separation buffer by 1 to 3 fold;

injecting a plug of the sample into the device; and applying an electric field across said sample and separation buffer.

2. The method of claim 1 wherein said sample comprises neutral analytes.

3. The method of claim 1 wherein said step of increasing the ionic strength of the sample includes the step of adding a salt to the sample.

4. The method of claim 1 wherein said step of increasing the ionic strength of the sample includes the step of adding conductive species not considered to be salts to the sample.

5. The method of claim 1 wherein said step of increasing the ionic strength of the sample includes the step of increasing the conductivity of the sample such that a component of the sample has a velocity such that it may act to form a boundary with the separation buffer.

6. The method of claim 1 wherein said step of applying an electric field causes the sample to form a boundary with the separation buffer.

7. The method of claim 1 wherein said step of applying an electric field causes field amplification in the separation buffer.

8. The method of claim 7 wherein said field amplification in the separation buffer causes stacking of separation buffer ions against the sample.

9. The method of claim 8 wherein said stacking of separation buffer ions against the sample causing stacking of sample components of the sample.

10. The method of claim 1 wherein said step of applying an electric field is carried out for a period of time sufficient to cause electrophoretic separation.

11. The method of claim 10 additionally comprising detecting said electrophoretic separation.

12. The method of claim 1 wherein said step of injecting a plug includes the step of injecting a plug with pressure.

13. The method of claim 1 wherein said step of injecting a plug includes the step of injecting the plug with an electric field.

14. The method of claim 1 wherein said step of injecting includes the step of injecting a plug into one of a capillary and a microchannel.

15. A method, comprising:
filling a device with a separation buffer having a pseudo-stationary phase;
adjusting the conductivity of a sample of analytes relative to the separation buffer such that the sample has a higher degree of conductivity than the separation buffer;
injecting a plug of the sample into the device; and
applying an electric field across said sample and separation buffer.

16. The method of claim 15 wherein said sample comprises neutral analytes.

17. The method of claim 15 wherein said step of adjusting the conductivity of the sample relative to the separation buffer includes the step of adding at lease one salt to the separation buffer.

18. The method of claim 15 wherein said step of adjusting the conductivity of the sample includes the step of increasing the conductivity of the sample such that a component of the sample has a velocity such that it may act to form a boundary with the separation buffer.

19. The method of claim 15 wherein said step of adjusting the conductivity of the sample relative to the separation buffer includes the step of adding conductive species not considered to be salts to the sample.

20. The method of claim 15 wherein said step of adjusting the conductivity of the sample relative to the separation buffer includes the step of adding pH buffers to the sample.

21. The method of claim 15 wherein said step of adjusting the conductivity of the sample relative to the separation buffer includes the step of adding conductive species with higher electrophoretic mobilities than the electrophoretic mobility of the separation buffer ions to the sample.

22. The method of claim 15 wherein said step of adjusting the conductivity of the sample relative to the separation buffer includes the step of eliminating organic modifiers in the sample.

23. The method of claim 15 wherein said step of adjusting the conductivity of the sample relative to the separation buffer includes the step of reducing the concentration of salts in the separation buffer.

24. The method of claim 15 wherein said step of adjusting the conductivity of the sample relative to the separation buffer includes the step of eliminating salts in the separation buffer.

25. The method of claim 15 wherein said step of adjusting the conductivity of the sample relative to the separation buffer includes the step of reducing the concentration of conductive species not considered to be salts in the separation buffer.

26. The method of claim 15 wherein said step of adjusting the conductivity of the sample relative to the separation buffer includes the step of eliminating conductive species not considered to be salts in the separation buffer.

27. The method of claim 15 wherein said step of adjusting the conductivity of the sample relative to the buffer includes the step of reducing the concentration of pH buffering agents in the separation buffer.

28. The method of claim 15 wherein said step of adjusting the conductivity of the sample relative to the separation buffer includes the step of eliminating pH buffering agents in the separation buffer.

29. The method of claim 15 wherein said step of adjusting the conductivity of the sample relative to the separation buffer includes the step of maintaining conductive species with electrophoretic mobilities in the separation buffer which are lower than electrophoretic mobilities of conductive species in the sample.

30. The method of claim 15 wherein said step of adjusting the conductivity of the sample relative to the separation buffer includes the step of adding conductive species to the separation buffer which have lower electrophoretic mobilities than conductive species in the sample.

31. The method of claim 15 wherein said step of adjusting the conductivity of the sample relative to the separation buffer includes the step of eliminating conductive species from the separation buffer which have higher electrophoretic mobilities than conductive species in the sample.

32. The method of claim 15 wherein said step of adjusting the conductivity of the sample relative to the separation buffer includes the step of adding organic modifiers to the separation buffer.

33. The method of claim 15 wherein said step of applying an electric field causes the sample to form a boundary with the separation buffer.

34. The method of claim 15 wherein said step of applying an electric field causes field amplification in the separation buffer.

35. The method of claim 34 wherein said field amplification in the separation buffer causes stacking of buffer ions against the sample.

36. The method of claim 35 wherein said stacking of buffer ions against the sample causes stacking of sample components of the sample.

37. The method of claim 15 wherein said step of applying an electric field is carried out for a period of time sufficient to cause electrophoretic separation.

38. The method of claim 37 additionally comprising detecting said electrophoretic separation.

39. The method of claim 15 wherein said step of injecting a plug includes the step of injecting a plug with pressure.

40. The method of claim 15 wherein said step of injecting a plug includes the step of injecting the plug with an electric field.

41. The method of claim 15 wherein said step of injecting includes the step of injecting a plug into one of a capillary and a microchannel.

42. A method of electrophoresis, comprising:
   filling a device with a separation buffer having a pseudo-stationary phase;
   increasing the ionic strength of a sample of analytes relative to the separation buffer so that the ionic strength of the sample of analytes is equal to or greater than the ionic strength of the separation buffer by 1 to 3 fold;
   applying an electric field across the sample and the separation buffer for a period of time sufficient to inject a plug of the sample into the device;
   applying an electric field across said plug and separation buffer; and
   detecting electrophoretic separation.

43. The method of claim 42 wherein said sample comprises neutral analytes.

44. The method of claim 42 wherein said step of applying a first electric field is carried out for a period of time sufficient to inject a plug of a desired length.

45. The method of claim 42 wherein the step of increasing the ionic strength of the sample includes the step of adding at least one salt to the sample.

46. The method of claim 42 wherein said step of increasing the ionic strength of the sample includes the step of adding conductive species not considered to be salts to the sample.

47. The method of claim 42 wherein said step of increasing the ionic strength of the sample includes the step of increasing the conductivity of the sample such that a component of the sample has a velocity such that it may act to form a boundary with the separation buffer.

48. The method of claim 42 wherein said injection of a plug includes injecting a plug into one of a capillary and a microchannel.

49. A method of electrophoresis, comprising:
   filling a device with a separation buffer having a pseudo-stationary phase;
   adjusting the conductivity of a sample of analytes relative to the separation buffer such that the sample has a higher degree of conductivity than the separation buffer;
   applying a first electric field across the sample and the separation buffer for a period of time sufficient to inject a plug of the sample into the device;
   applying a second electric field across said plug and separation buffer; and
   detecting electrophoretic separation.

50. The method of claim 49 wherein said sample comprises neutral analytes.

51. The method of claim 49 wherein said step of applying a first electric field is carried out for a period of time sufficient to inject a plug of a desired length.

52. The method of claim 49 wherein the step of adjusting the conductivity of the sample includes the step of adding at least one salt to the sample.

53. The method of claim 49 wherein said step of adjusting the conductivity of the sample includes the step of increasing the conductivity of the sample such that the sample has two to four times the conductivity of the buffer.

54. The method of claim 49 wherein said step of adjusting the conductivity of the sample relative to the buffer includes the step of adding conductive species not considered to be salts to the sample.

55. The method of claim 49 wherein said step of adjusting the conductivity of the sample relative to the buffer includes the step of adding pH buffers to the sample.

56. The method of claim 49 wherein said step of adjusting the conductivity of the sample relative to the buffer includes the step of adding conductive species with higher electrophoretic mobilities than the electrophoretic mobility of the buffer ions to the sample.

57. The method of claim 49 wherein said step of adjusting the conductivity of the sample relative to the separation buffer includes the step of eliminating organic modifiers in the sample.

58. The method of claim 49 wherein said step of adjusting the conductivity of the sample relative to the separation buffer includes the step of reducing the concentration of salts in the separation buffer.

59. The method of claim 49 wherein said step of adjusting the conductivity of the sample relative to the separation buffer includes the step of eliminating salts in the separation buffer.

60. The method of claim 49 wherein said step of adjusting the conductivity of the sample relative to the separation buffer includes the step of reducing the concentration of conductive species not considered to be salts in the separation buffer.

61. The method of claim 49 wherein said step of adjusting the conductivity of the sample relative to the separation buffer includes the step of eliminating conductive species not considered to be salts in the separation buffer.

62. The method of claim 49 wherein said step of adjusting the conductivity of the sample relative to the separation buffer includes the step of reducing the concentration pH buffering agents in the separation buffer.

63. The method of claim 49 wherein said step of adjusting the conductivity of the sample relative to the separation buffer includes the step of eliminating pH buffers in the separation buffer.

64. The method of claim 49 wherein said step of adjusting the conductivity of the sample relative to the separation buffer includes the step of maintaining conductive species with electrophoretic mobilities in the separation buffer which are lower than electrophoretic mobilities of conductive species in the sample.

65. The method of claim 49 wherein said step of adjusting the conductivity of the sample relative to the separation buffer includes the step of adding conductive species to the separation buffer which have lower electrophoretic mobilities than conductive species in the sample.

66. The method of claim 49 wherein said step of adjusting the conductivity of the sample relative to the separation buffer includes the step of eliminating conductive species from the separation buffer which have higher electrophoretic mobilities than conductive species in the sample.

67. The method of claim 49 wherein said step of adjusting the conductivity of the sample relative to the separation buffer includes the step of adding organic modifiers to the separation buffer.

68. The method of claim 49 wherein said injection of a plug includes injecting a plug into one of a capillary and a microchannel.

69. A method for electrokinetic sample stacking of analytes, comprising:

filling a device with a separation buffer having a pseudo-stationary phase;

providing a sample of analytes with a:higher ionic strength than the ionic strength of the separation buffer;

electrokinetically injecting a plug of the sample into the device; and applying an electric field across said plug and separation buffer to cause separation.

70. The method of claim 69 wherein said sample comprises neutral analytes.

71. The method of claim 69 wherein said step of providing a sample of analytes such that the sample has a higher ionic strength includes the step of adding at least one salt to the sample.

72. The method of claim 69 wherein said step of providing a sample of analytes such that the sample has a higher ionic strength includes the step of adding conductive species not considered to be salts to the sample.

73. The method of claim 69 wherein said step of providing a sample of analytes such that the sample has a higher ionic strength includes the step of increasing the conductivity of the sample such that a component of the sample has a velocity such that it may act to form a boundary with the separation buffer.

74. The method according to claim 69 wherein said step of applying an electric field across said high-salt sample and separation buffer causes micellar stacking.

75. The method as claimed in claim 74 further comprising detecting the micellar stacking by UV absorbance at 242 nm with a 20 nm bandwidth.

76. The method according to claim 69 wherein the step of injecting includes the step of injecting a plug into one of a capillary and a microchannel.

77. The method according to claim 69 wherein the step of injecting includes the step of injecting a plug into any type of electrophoretic device.

78. The method according to claim 69 further comprising a step of detecting the separation.

79. The method according to claim 78 wherein the step of detecting the separation includes a step of detecting through the use of a fluorescence detector.

80. The method as claimed in claim 69 wherein the step of filling a device with a separation buffer includes a step of first electrophoretically conditioning the device.

81. The method as claimed in claim 69 wherein the step of electrokinetically injecting a plug of the sample occurs by applying an electric field across said sample and separation buffer of approximately +250/−1000 kV for approximately 20 to 120 seconds.

82. The method as claimed in claim 69 wherein said step of applying an electric field across said sample and separation buffer to cause separation includes applying an electric field of approximately +500/−2000 kV.

* * * * *

UNITED STATES PATENT AND TRADEMARK OFFICE
CERTIFICATE OF CORRECTION

PATENT NO. : 6,569,305 B1
DATED : May 27, 2003
INVENTOR(S) : Palmer et al.

It is certified that error appears in the above-identified patent and that said Letters Patent is hereby corrected as shown below:

Title page,
Please insert between Item [76], Inventors and Item [*] Notice, the following item:
-- [73]  Assignee:  University of Pittsburgh of the Commonwealth System of Higher Education, Pittsburgh, PA (US) --

Signed and Sealed this

Second Day of March, 2004

JON W. DUDAS
*Acting Director of the United States Patent and Trademark Office*